United States Patent
Van Zyl et al.

(10) Patent No.: US 8,940,505 B2
(45) Date of Patent: Jan. 27, 2015

(54) **PRODUCTION OF HETEROLOGOUS EXTRACELLULAR POLYPEPTIDES IN *YARROWIA LIPOLYTICA***

(75) Inventors: Petrus Jackobus Van Zyl, Pretoria (ZA); Mulalo Bethuel Nthangeni, Kempton Park (ZA); Faranani Ramagoma, Bronkhorstspruit (ZA)

(73) Assignee: CSIR, Pretoria (ZA)

( * ) Notice: Subject to any disclaimer, the term of this patent is extended or adjusted under 35 U.S.C. 154(b) by 0 days.

(21) Appl. No.: 14/111,122

(22) PCT Filed: Apr. 12, 2012

(86) PCT No.: PCT/IB2012/051784
§ 371 (c)(1),
(2), (4) Date: Dec. 23, 2013

(87) PCT Pub. No.: WO2012/140588
PCT Pub. Date: Oct. 18, 2012

(65) Prior Publication Data
US 2014/0127748 A1 May 8, 2014

(30) Foreign Application Priority Data
Apr. 12, 2011 (GB) .................................. 1106188.4

(51) Int. Cl.
| | |
|---|---|
| *C12P 21/02* | (2006.01) |
| *C12N 9/20* | (2006.01) |
| *C12N 1/16* | (2006.01) |
| *C12N 9/12* | (2006.01) |
| *C12N 9/14* | (2006.01) |

(52) U.S. Cl.
CPC *C12N 9/20* (2013.01); *C07N 14/39* (2013.01); *C12N 1/16* (2013.01); *C12N 9/1205* (2013.01); *C12P 21/02* (2013.01); *C12N 9/14* (2013.01)
USPC ...................... 435/69.1; 435/254.11; 435/483

(58) Field of Classification Search
None
See application file for complete search history.

(56) References Cited

FOREIGN PATENT DOCUMENTS

EP 0220864 5/1987

OTHER PUBLICATIONS

Benachour et al., "Deletion of GPI7, a yeast gene required for addition of a side chain to the glycosylphosphatidylinositol (GPI) core structure, affects GPI protein transport, remodeling, and cell wall integrity" Journal of Biological Chemistry, 274(21):15251-15261 (1999).
Madzak et al. "*Heterologous protein expression and secretion in the non-conventional yeast Yarrowia lipolytica*"J Biotechnol. 109(1-2):63-81 (2004).
Maharajh et al. "*Multi-copy expression and fed-batch production of Rhodotorula araucariae epoxide hydrolase in Yarrowia lipolytica*" Appl Microbiol Biotechnol. 79(2):235-44 (2008).
Mauersberger et al. "Insertional mutagenesis in the n-alkane-assimilating yeast *Yarrowia lipolytica*: generation of tagged mutations in genes involved in hydrophobic substrate utilization" J Bacteriol. 183(17):5102-9 (2001).
Nthangeni et al. "*Development of a versatile cassette for directional genome walking using cassette ligation-mediated PCR and its application in the cloning of complete lipolytic genes from Bacillus species*" J Microbiol Methods. 61(2):225-34 (2005).
Pitter et al., "*Biosynthesis and function of GPI proteins in the yeast Saccharomyces cerevisiae*" Biochimica and Biophysica Acta, 1771(3): 405-420 (2007).
Richard et al., "*Tagging morphogenetic genes by insertional mutagenesis in the yeast Yarrowia lipolytica*" Journal of Bacteriology, 183 (10): 3098-3107 (2001).
Winkler et al., "*Glycogen, hyaluronate, and some other polysaccharides greatly enhance the formation of exolipase by Serratia marcescens*"J Bacteriol. 138(3): 663-70 (1979).

*Primary Examiner* — Jim Ketter
(74) *Attorney, Agent, or Firm* — Riverside Law LLP

(57) ABSTRACT

This invention relates to protein and/or polypeptide production, particularly improved production of extracellular heterologous polypeptides and proteins. In particular, the invention relates to compositions of cell populations capable of improved levels of extracellular secretion relative to control populations, kits containing such compositions, methods of producing heterologous proteins of interest and recombinant microorganisms capable of improved extracellular heterologous protein production.

12 Claims, 5 Drawing Sheets

SEQUENCE LISTING

```
<160> NUMBER OF SEQ ID NOS: 8

<210> SEQ ID NO 1
<211> LENGTH: 31
<212> TYPE: DNA
<213> ORGANISM: Yarrowia lipolytica

<400> SEQUENCE: 1
gagtagtggc aagcttgtcc tccaccgttt g                          31

<210> SEQ ID NO 2
<211> LENGTH: 34
<212> TYPE: DNA
<213> ORGANISM: Yarrowia lipolytica

<400> SEQUENCE: 2
gttgacgttt gtgtccaact ggattggccc tctg                       34

<210> SEQ ID NO 3
<211> LENGTH: 36
<212> TYPE: DNA
<213> ORGANISM: Yarrowia lipolytica

<400> SEQUENCE: 3
gtggcaagct tgtcctccac cgtttgacac attatc                     36

<210> SEQ ID NO 4
<211> LENGTH: 40
<212> TYPE: DNA
<213> ORGANISM: Yarrowia lipolytica

<400> SEQUENCE: 4
gattaccctg ttatccctta gcgtcaggtt gcagggtctg                 40

<210> SEQ ID NO 5
<211> LENGTH: 40
<212> TYPE: DNA
<213> ORGANISM: Yarrowia lipolytica

<400> SEQUENCE: 5
```

```
ctagggataa cagggtaatg attggcctttt acgagaatgt                    40

<210> SEQ ID NO 6
<211> LENGTH: 34
<212> TYPE: DNA
<213> ORGANISM: Yarrowia lipolytica

<400> SEQUENCE: 6
gagttgtacc aggtagtagg ataggcggtg gagg                           34

<210> SEQ ID NO 7
<211> LENGTH: 26
<212> TYPE: DNA
<213> ORGANISM: Yarrowia lipolytica

<400> SEQUENCE: 7
cacggatcca tgctctggaa aaggtc                                    26

<210> SEQ ID NO 8
<211> LENGTH: 29
<212> TYPE: DNA
<213> ORGANISM: Yarrowia lipolytica

<400> SEQUENCE: 8
catcatcatc atcatttaca ccgatctat                                 29
```

PRODUCTION OF HETEROLOGOUS EXTRACELLULAR POLYPEPTIDES IN YARROWIA LIPOLYTICA

CROSS-REFERENCE TO RELATED APPLICATIONS

This application is the U.S. national phase application filed under 35 U.S.C. §371 claiming benefit to International Patent Application No. PCT/IB2012/051784, filed on Apr. 12, 2012, which is entitled to priority to GB 1106188.4, filed Apr. 12, 2011, each of which applications is hereby incorporated herein by reference in their entireties.

INTRODUCTION

This invention relates to protein and/or polypeptide production, particularly improved production of extracellular heterologous polypeptides and proteins. In particular, the invention relates to compositions of cell populations capable of improved levels of extracellular secretion relative to control populations, kits containing such compositions, methods of producing heterologous proteins of interest and recombinant microorganisms capable of improved extracellular heterologous protein production.

BACKGROUND OF THE INVENTION

*Yarrowia lipolytica* is a non-conventional yeast which has been awarded the Generally Regarded As Safe (GRAS) status by the American Food and Drug Administration (FDA). The GRAS rating of *Y. lipolytica* makes it suited for the production of bioactive proteins and polypeptides for human applications (Madzak et al., 2004).

Like most other eukaryotes, *Yarrowia lipolytica* harbors a GPI anchoring machinery and uses it to attach proteins to membranes. Although a few GPI proteins reside permanently at the plasma membrane, a majority of them are further processed and are integrated into the cell wall by a covalent attachment to cell wall glucans.

The GPI biosynthetic pathway is necessary for growth and survival of yeast cells. The GPI lipids are synthesized in the endoplasmic reticulum and added onto proteins by a pathway comprising 12 steps, carried out by 23 gene products, 19 of which are essential. It is estimated that some 60 GPI proteins are predicted from their genomic sequences to serve enzymatic functions required for the biosynthesis and the continuous shape adaptations of the cell wall, others appear to form structural elements of the cell wall and yet others mediate cell adhesion (Benachour et al., 1999).

The prior art teaches that there is no single factor that will improve the production of all heterologous proteins. As a result, there is a need in the art for identifying improved large-scale expression systems capable of secreting extracellular recombinant polypeptides.

SUMMARY OF THE INVENTION

The present invention provides compositions and methods for improving secretion of heterologous protein from a population of *Yarrowia lipolytica*-derived cells. The compositions comprise host cell populations that have been genetically modified to increase secretion of a heterologous protein of interest into the extracellular space. The genetically modified host cell populations are useful for improving the extracellular secretion of any protein or polypeptide of interest, including therapeutic proteins, hormones, growth factors, extracellular receptors or ligands, proteases, kinases, blood proteins, chemokines, cytokines, antibodies and the like. In various embodiments, the modified *Yarrowia lipolytica* host cell populations comprise one or more genomic mutations responsible for or contributing to the improved level of extracellular secretion of the heterologous protein of interest.

The present invention teaches that deletion of the gpi7 gene from *Yarrowia lipolytica* results in Increased secretion of heterologous proteins and polypeptides into a culture medium. Further, the modified microorganisms and methods described in this invention provide a significant advancement for the potential production of heterologous proteins and polypeptides for industrial and therapeutic purposes.

According to a first aspect of the present invention, there is provided for a composition comprising a *Yarrowia lipolytica*-derived (Accession No. NCIMB 42022, deposited on 9 Aug. 2012 at National Collection of Industrial Food and Marine Bacteria (NCIMB Ltd), of Ferguson Building, Craibstone Estate, Bucksburn, Aberdeen, AB21 9YA, Scotland) cell population capable of expressing a heterologous polypeptide of interest, wherein the level of extracellular secretion of the heterologous polypeptide is increased relative to the level of extracellular secretion of the heterologous polypeptide by a control *Yarrowia lipolytica* cell population (Accession No. NCIMB 42021, deposited on 9 Aug. 2012 at National Collection of Industrial Food and Marine Bacteria (NCIMB Ltd), of Ferguson Building, Craibstone estate, Bucksburn, Aberdeen, AB21 9YA, Scotland), wherein the *Yarrowia lipolytica*-derived cell population has at least one genomic modification relative to the control *Yarrowia lipolytica* cell population, and wherein the genomic modification is attributable to the increase in extracellular secretion.

In a preferred embodiment of this aspect of the invention the *Yarrowia lipolytica*-derived cell population includes an expression cassette comprising a polynucleotide encoding a heterologous polypeptide.

Preferably the heterologous polypeptide is for use in industrial and/or therapeutic applications.

Preferably the genomic modification of the *Yarrowia lipolytica*-derived cell population affects one or more genes involved in glycosylphosphatidylinositol (GPI) anchoring.

More preferably the genomic modification includes the deletion or disruption of the gene encoding the GPI7 anchor protein.

The *Yarrowia lipolytica*-derived cell population containing the genomic modification preferably secretes heterologous polypeptides extracellularly at a rate of at least two times the level of extracellular secretion from the control *Yarrowia lipolytica*-derived cell population.

According to a second aspect of the present invention, there is provided for a kit comprising the *Yarrowia lipolytica* composition described above.

According to a third aspect of the present invention, there is provided for a method of producing a heterologous polypeptide of interest comprising obtaining a *Yarrowia lipolytica*-derived cell population which includes an expression cassette encoding a heterologous polypeptide of interest and culturing the cell population under conditions suitable for the expression of the heterologous polypeptide of interest wherein the *Yarrowia lipolytica*-derived cell population of this embodiment has at least one genomic modification relative to a control *Yarrowia lipolytica*-derived cell population and wherein the genomic modification results in an increase in the extracellular secretion of the heterologous polypeptide of interest.

A fourth aspect of the present invention provides a method for increasing the extracellular secretion of a polypeptide of interest in *Yarrowia lipolytica* strains wherein the increased extracellular secretion of the polypeptide into a culture medium through the cell membrane is triggered by affecting one or more genes involved in glycosylphosphatidylinositol (GPI) anchoring, preferably the gene encoding GPI7.

According to a fifth aspect of the present invention, a recombinant microorganism is provided which microorganism has been genomically modified such that one or more of the genes involved in glycosylphosphatidylinositol (GPI) anchoring are affected, the microorganism being further transformed with a recombinant vector comprising a target polypeptide-encoding gene and wherein the microorganism is capable of expressing the target polypeptide, which is secreted extracellularly. The recombinant microorganism is preferably *Yarrowia lipolytica*. More preferably the affected gene is the gene encoding GPI7.

According to a sixth aspect of the present invention a method for the extracellular secretion of a target polypeptide is disclosed, the method comprising the steps of culturing a recombinant microorganism to express a target polypeptide which is then secreted to the outside of the microbial cell and into a culture medium, and recovering the target polypeptide from the culture medium.

It will be appreciated that the extracellular secretion of the target polypeptide in this invention will not accompany lysis of the microorganism.

BRIEF DESCRIPTION OF THE FIGURES

Non-limiting embodiments of the invention will now be described by way of example only and with reference to the following figures.

(B) Samples (10 μL of crude supernatant) were resolved by SDS-PAGE (12.5%). Sizes of prestained Pageruler™ page ruler protein ladder (Fermentas) molecular weight standards in KDa (lane M) are indicated on the left. The arrow marks the 38.5 kDa band representing LIP2.

Figure 5:
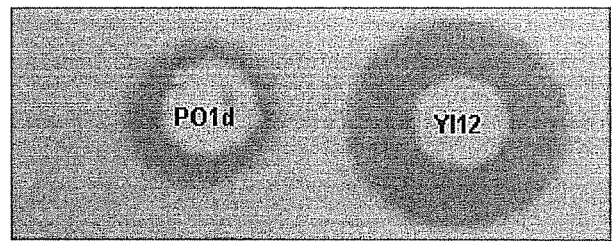

FIG. 5: Hyperproduction of LIP2 on YNBT by the *Y. lipolytica* Δylgpi7 (YI12) strain and the *Y. lipolytica* Po1d control strain (Po1d). Extracellular lipase activity detection was performed on YNBT plates and the hydrolysis/colony diameter was measured after 48 h.

Figure 6:
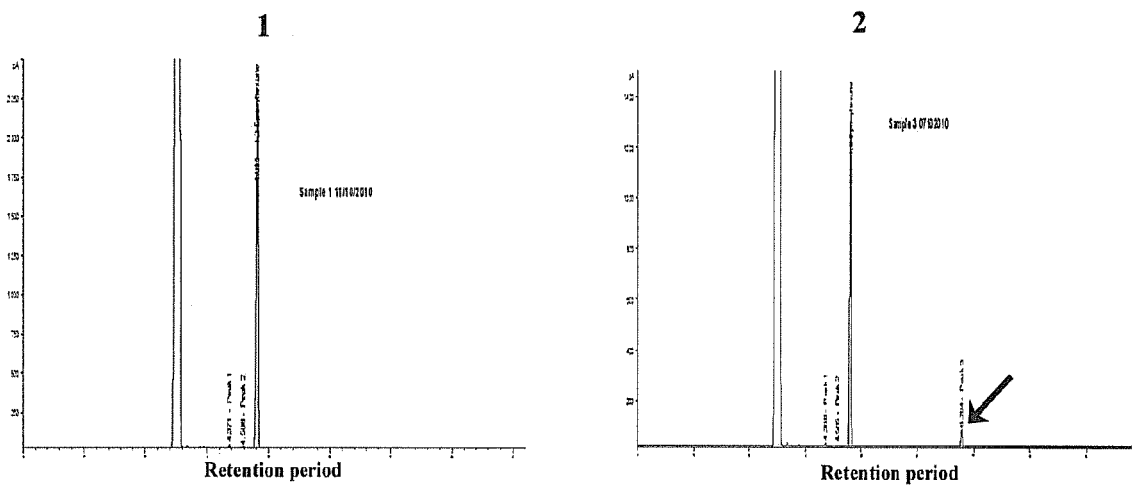

FIG. 6: Analysis of EH production by the *Y. lipolytica* YI25HmA strain and YI25HmAΔGPI7 strain. Crude extracellular fractions were mixed with 1,2-epoxyhexane and analysed by GC. The chromatograms illustrate the GC peaks generated by *Y. lipolytica* (1) YI25HmA and (2) YI25HmAΔGPI7. The arrow indicates the 1,2-hexanediol peak.

Figure 7:
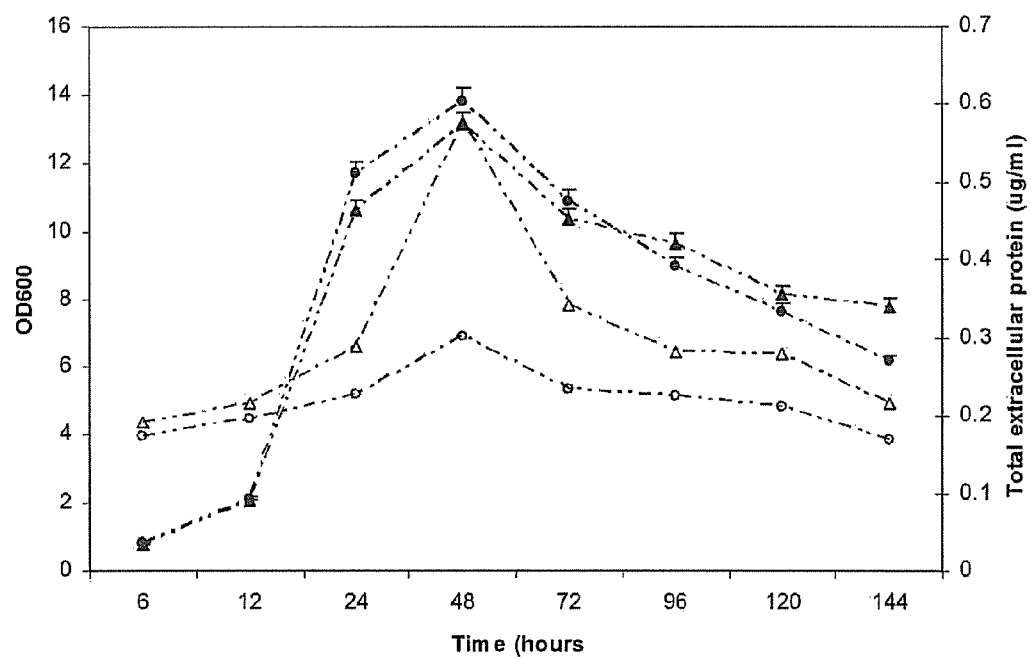

FIG. 7: Extracellular protein accumulation in cultures of the *Y. lipolytica* YI25HmA and YI25HmAΔGPI7 strains. Solid circles (●) represent the growth profile of the *Y. lipolytica* YI25HmA strain while solid triangles (▲) represent the growth profile of the YI25HmAΔGPI7 strain. Extracellular protein accumulation from the *Y. lipolytica* YI25HmA strain is represented by the open circles (○), while extracellular protein accumulation from the YI25HmAΔGPI7 strain is represented by the open triangles (Δ). Error bars represent the mean standard deviation calculated from three independent experiments.

DETAILED DESCRIPTION OF THE INVENTION

The present invention will now be described more fully hereinafter with reference to the accompanying drawings, in which some, but not all embodiments of the invention are shown.

The invention as described should not to be limited to the specific embodiments disclosed and modifications and other embodiments are intended to be included within the scope of the invention. Although specific terms are employed herein, they are used in a generic and descriptive sense only and not for purposes of limitation.

The term "protein" for example, should be read to include "peptide" and "polypeptide" and vice versa. The term "secrete" or "secretion" includes active or passive passage of the heterologous protein from the intracellular space to the extracellular space.

Provided herein are multiple *Yarrowia lipolytica* cell populations that result in an increase in the level of extracellular secretion of heterologous protein compared to the increase in extracellular secretion by a wildtype *Yarrowia lipolytica* strain. "Wildtype" generally refers to control strain wherein the gpi7 gene is intact (functions normally). "Heterologous," "heterologously expressed," or "recombinant" generally refers to a gene or protein that is not endogenous to the host cell or is not endogenous to the location in the native genome in which it is present, and has been added to the cell by infection, transfection, transformation, microinjection, electroporation, microprojection, or the like. A "*Yarrowia lipolytica*-derived cell" is a cell that has been modified to introduce genomic changes in a *Yarrowia lipolytica* cell. The genomic changes may be introduced by way of any number of mutagenesis or genetic engineering strategies known in the art.

The *Yarrowia lipolytica* host cell populations of the invention secrete a greater proportion of recombinant protein or polypeptide into the extracellular space compared to the level of secretion from a control or wildtype cell population. The increase in extracellular secretion is attributable to one or more genomic alterations in the improved cell population in comparison to the control cell population. By "attributable to" in this context is intended that the genomic alteration(s) is(are) directly or indirectly responsible for the increase in extracellular secretion. Thus, an improved cell population having one or more genomic alterations attributing to the increase in extracellular secretion will exhibit an increased level of secretion of a heterologous protein or polypeptide compared to the level of secretion from an otherwise genetically identical cell population expressing the same heterologous protein.

The improved secretion is the result of one or more genomic alterations in the *Yarrowia lipolytica*-derived cells affecting one or more genes in the GPI biosynthetic pathway. In particular, the GPI7 polypeptide is notable for its role in the synthesis of cell wall and cell membrane proteins.

In the present invention it was determined that disruption or deletion of the gpi7 gene from *Yarrowia lipolytica* resulted in increased secretion of cell membrane targeted proteins into a culture medium.

A heterologous protein of interest can be produced in one or more of the improved host cells disclosed herein by introducing into the host cell an expression vector encoding the heterologous protein of interest. In one embodiment, the vector comprises a polynucleotide sequence encoding the protein of interest operably linked to a promoter capable of functioning in the chosen host cell, as well as all other required transcription and translation regulatory elements. The term "operably linked" refers to any configuration in which the transcriptional and any translational regulatory elements are covalently attached to the encoding sequence in such disposition(s), relative to the coding sequence, that in and by action of the host cell, the regulatory elements can direct the expression of the coding sequence. The heterologous protein of interest can be expressed from polynucleotides in which the heterologous polypeptide coding sequence is operably linked to transcription and translation regulatory elements to form a functional gene from which the host cell can express the protein or polypeptide. The coding sequence for the protein or polypeptide of interest can be a native coding sequence for the polypeptide, if available, but will more preferably be a coding sequence that has been selected, improved, or optimized for use in an expressible form in the strains of the invention: for example, by optimizing the gene to reflect the codon use bias of *Yarrowia lipolytica*.

Other regulatory elements may be included in the expression vector (also termed "expression construct" or "expression cassette").

Following genomic alteration, the cells can be grown as independent colonies (e.g., by streaking the cells onto a solid or semi-solid media such as agar), picked, and inoculated into fresh media. The individual colonies can be cultured under suitable conditions for expression of the heterologous protein or polypeptide of interest, and cell-free extracts obtained from the culture to identify strains having improved extracellular secretion.

For the purposes of the present invention, the term "increased" or "improved" in the context of extracellular secretion is relative to the level of protein or polypeptide that is secreted into the extracellular space when the protein or polypeptide of interest is expressed in one or more control cell populations. In one embodiment, the improved host cell population secretes into the extracellular media at least 0.1 mg of the heterologous protein of interest per ml of cell culture media when expressed at an optical cell density of at least 40 mg/mL, when grown (i.e. within a temperature range of about 4 deg. C. to about 55 deg. C., including about 10 deg. C., about 15 deg. C., about 20 deg. C., about 25 deg. C., about 30 deg. C., about 35 deg. C., about 40 deg. C., about 45 deg. C., and about 50 deg. C.) in a mineral salts medium. In another embodiment, the improved strain secretes 0.1 to 10 mg/mL protein, or at least about 0.2, about 0.3, about 0.4, about 0.5, about 0.6, about 0.7, about 0.8, about 0.9 or at least about 1.0 mg/mL protein. In one embodiment, the total protein or polypeptide of interest produced by the improved host cell population of the invention is at least 1.0 mg/mL, at least about 2 mg/mL, at least about 3 mg/mL, about 4 mg/mL, about 5 mg/mL, about 6 mg/mL, about 7 mg/mL, about 8 mg/mL, about 10 mg/mL, about 15 mg/mL, about 20 mg/mL, at least about 25 mg/mL, or greater. In some embodiments, the amount of heterologous protein of interest that is secreted to the extracellular space is at least about 5%, about 10%, about 15%, about 20%, about 25%, about 30%, about 40%, about 50%, about 60%, about 70%, about 80%, about 90%, about 95%, about 96%, about 97%, about 98%, about 99%, or more of the total heterologous protein of interest produced by the cell population. In another embodiment, the improved host cell population secretes at least about 50%, at least about 75%, at least about 100%, at least about 150%, at least about 2-fold, at least about 3-fold, at least about 4-fold or more of the protein of interest into the extracellular space when compared to a control cell population. In one embodiment, the improvement in secretion is determined based on the amount or activity of the protein of interest.

If desired, the proteins and/or polypeptides produced using one or more strains according to this invention may be isolated and purified to substantial purity by standard techniques well known in the art, including, but not limited to, ammonium sulfate or ethanol precipitation, centrifugation, filtration, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilisation, selective precipitation with such substances as column chromatography, immunopurification methods, and others.

The cell growth conditions for the host cells described herein include that which facilitates expression of the protein of interest in the improved *Yarrowia lipolytica* cell population described herein, and/or that which facilitates fermentation of the expressed protein of interest. As used herein, the term "fermentation" includes both embodiments in which literal fermentation is employed and embodiments in which other, non-fermentative culture modes are employed. Growth, maintenance, and/or fermentation of the populations of improved host cells described herein may be performed at any scale. In one embodiment, the fermentation medium may be selected from among rich media, minimal media, and mineral salts media.

Mineral salts media consists of mineral salts and a carbon source such as, e.g., glucose, sucrose, or glycerol. The mineral salts used to make mineral salts media include those selected from among, e.g., potassium phosphates, ammonium sulfate or chloride, magnesium sulfate or chloride, and trace minerals such as calcium chloride, borate, and sulphates of iron, copper, manganese, and zinc.

In the present invention, growth, culturing, and/or fermentation of the transformed host cells is performed within a temperature range permitting survival of the host cells, preferably a temperature within the range of about 4 deg. C. to about 55 deg. C., inclusive, preferably not more than about 30 to 34 deg. C. Thus, e.g., the terms "growth" (and "grow," "growing"), "culturing" (and "culture"), and "fermentation" (and "ferment," "fermenting"), as used herein in regard to the host cells of the present invention, inherently means "growth," "culturing," and "fermentation," within a temperature range of about 4 deg. C. to about 55 deg. C., inclusive, preferably not more than about 34 deg. C. In addition, "growth" is used to indicate both biological states of active cell division and/or enlargement, as well as biological states in which a non-dividing and/or non-enlarging cell is being metabolically sustained, the latter use of the term "growth" being synonymous with the term "maintenance." The host cells of the invention should be grown and maintained at a suitable temperature for normal growth of that cell type. Such normal growth temperatures may be readily selected based on the known growth requirements of the host cell. Preferably, during the establishment of the culture and particularly during course of the screening, the cell culture is incubated in a controlled humidity suitable for growth of the selected cells before and after transformation with the heterologous protein or polypeptide of interest. The humidity of the incubation is controlled to minimize evaporation from the culture vessel, and permit the use of smaller volumes. Alternatively, or in addition to controlling humidity, the vessels may be covered with lids in order to minimize evaporation. Selection of the incubation temperature depends primarily upon the Identity of the host cells utilized. Selection of the percent humidity to control evaporation is based upon the selected volume of the vessel and concentration and volume of the cell culture in the vessel, as well as upon the incubation temperature. Thus, the humidity may vary from about 10% to about 80%. It should be understood that selection of suitable conditions is well within the skill of the art.

The methods and compositions of the present invention are useful for the expression and extracellular secretion of high levels of a properly processed protein or polypeptide of interest. The improved host cell populations described herein are useful for production of a protein or polypeptide of interest of any species and of any size. The protein or polypeptide of interest may be a therapeutically useful protein or polypeptide.

The present invention also provides kits useful for expression and extracellular secretion of a heterologous protein or polypeptide of interest. The kit comprises one or more of the improved *Yarrowia lipolytica* host cell populations described herein. These kits may also comprise reagents sufficient to facilitate growth and maintenance of the cell populations as well as reagents and/or constructs for expression of a heterologous protein or polypeptide of interest. The populations of host cells may be provided in the kit in any manner suitable for storage, transport, and reconstitution of cell populations. The cell populations may be provided live in a tube, on a plate, or on a slant, or may be preserved either freeze-dried or frozen in a tube or vial. The cell populations may contain additional components in the storage media such as glycerol, sucrose, albumin, or other suitable protective or storage agents.

The following examples are offered by way of illustration and not by way of limitation.

Cell Lines (Strains)

*Y. lipolytica* strains

TABLE 1

| Po1d | A positive control *Y. lipolytica* strain in which the gpi7 gene is intact (functions normally); National Institute for Agricultural Research, France (INRA), UMR Microbiologie et Génétique Moléculaire (CLIB139) |
| --- | --- |
| Δylgpi7 | A *Y. lipolytica* strain in which the gpi7 gene has been deleted; generated in this study |
| Yl25HmA | A *Y. lipolytica* strain described in Maharajh et al., 2008 which over-expresses an epoxide hydrolase (EH) enzyme intracellularly; generated in this study |
| Yl25HmAΔGPI7 | Yl25HmA in which the gpi7 gene has been deleted; generated in this study |

Media Compositions Used in Yeast Cell Culture

TABLE 2

| Medium | Components |
| --- | --- |
| YNBcasa plates | 1.7 g · L$^{-1}$ YNB without amino acids and (NH$_4$)$_2$SO4, 0.2% w/v casamino acids, 4 g · L$^{-1}$ NH$_4$Cl, 20 g · L$^{-1}$ glucose, 15 g · L$^{-1}$ Agar |
| YNB$_{5000}$ plates | 1.7 g · L$^{-1}$ YNB without amino acids and (NH$_4$)$_2$SO4, 4 g · L$^{-1}$ NH$_4$Cl, 20 g · L$^{-1}$ glucose, 15 g · L$^{-1}$ Agar |
| YPD broth | 20 g · L$^{-1}$ peptone, 20 g · L$^{-1}$ glucose and 10 g · L$^{-1}$ yeast extract |
| YPD plates | 20 g · L$^{-1}$ peptone, 20 g · L$^{-1}$ glucose and 10 g · L$^{-1}$ yeast extract, 15 g · L$^{-1}$ Agar |
| YPDO medium | 20 g · L-$^{1}$ peptone, 20 g · L$^{-1}$ glucose, 10 g · L$^{-1}$ yeast extract, 10 g · L$^{-1}$ of olive oil |
| YNBT plates | 1.7 g · L$^{-1}$ of YNB without (NH$_4$)$_2$SO4 and amino acids, 4 g · L$^{-1}$ NH4Cl, 10 g · L$^{-1}$ of tributyrin |

Plasmid DNA (Vectors)

pGemT-Easy™ Promega (www.promega.com)

JMP115—National Institute for Agricultural Research, France (INRA), UMR Microbiologie et Génétique Moléculaire pRRQ2—cre-expressing plasmid; National Institute for Agricultural Research, France (INRA), UMR Microbiologie et Génétique Moléculaire Oligonucleotides (Primers)

TABLE 3

| | Oligonucleotide Name | 5'-3' Sequence | Corresponding Region/Comments |
| --- | --- | --- | --- |
| 1. | YI3485356F | GAGTAGTGGCAAGCTTGTCCTCCACCGTTTG (SEQ ID NO: 1) | 5' of border region |
| 2. | YI3487261R | GTTGACGTTTGTGTCCAACTGGATTGGCCCTCTG (SEQ ID NO: 2) | 3' of border region |
| 3. | GPI7 Promoter Forward PF | GTGGCAAGCTTGTCCTCCACCGTTTGACACATTATC (SEQ ID NO: 3) | 5' of GPI7 promoter region |
| 4. | GPI7 Promoter Reverse PR | <u>GATTACCCTGTTATCCCTTAG</u>CGTCAGGTTGCAGGGTCTG (SEQ ID NO: 4) | 3' of GPI7 promoter region; containing a I-Sce-I restriction site |
| 5. | GPI7 Terminator Forward TF | C<u>TAGGGATAACAGGGTAAT</u>GATTGGCCTTTACGAGAATGT (SEQ ID NO: 5) | 5' of GPI7 terminator region; containing a I-SceI-restriction site |

TABLE 3-continued

| Oligonucleotide Name | 5'-3' Sequence | Corresponding Region/Comments |
|---|---|---|
| 6. GPI7 Terminator Reverse TR | GAGTTGTACCAGGTAGTAGGATAGGCGGTGGAGG (SEQ ID NO: 6) | 3' of GPI7 terminator region |
| 7. GPI7F | CACGGATCCATGCTCTGGAAAAGGTC (SEQ ID NO: 7) | 5' of gpi7 ORF |
| 8. GPI7R | CATCATCATCATCATTTACACCGATCTAT (SEQ ID NO: 8) | 3' of gpi7 ORF |

Random Mutagenesis and Identification of the Gene of Interest

The initial study involved transformation of *Y. lipolytica* Po1d with a vector (Mauersberger et al., 2001) that integrates randomly into the genome. Transformants were first selected on YNBT media based on extracellular *lipolytica* activity before identifying the integration locus (sequencing). Oligonucleotide primers were designed to clone the regions bordering the integrated vector. The upstream and downstream borders were amplified using cassette-ligation mediated PCR described previously (Nthangeni et al., 2005). The DNA fragments obtained by PCR amplifications were ligated into pGemT-Easy and sequenced. To confirm that the vector integrated at the identified region, FOR was performed using primers YI3485356F and YI3487261R. Nucleotide sequences were analysed using Chromas 2.33 (http://www-.technelysium.com.au/chromas.html). Real-Time PCR was also performed to confirm that the disrupted gene was that coding for gpi7.

Construction of Deletion Cassettes

Promoter-Terminator (PT) Cassette Construction

The promoter-terminator (PT) cassette was obtained in a two-step PCR reaction in which first the promoter (P) and terminator (T) regions of gpi7 were separately amplified. The combined P and T PCR products were then used as templates in a second PCR reaction to obtain the full gpi7 PT PCR (2200 bp) products. The gpi7 PT PCR products were subsequently cloned into a pGemT-Easy vector. The PCR product was cloned using the T-overhangs of a linear pGemT-Easy vector. Verification of the constructs was carried out by restriction digestion with EcoRI as well as sequence analysis using T7 and SP6 promoter primers. Comparisons were done by BLAST search against the *Y. lipolytica* RST and genome databases at the genolevures site (http://cbi.labri.fr/Genolevures and at http://www.ncbi.nlm.nih.gov/BLAST/).

Construction of the Promoter-Hph-Terminator (PHT) Cassette

The deletion cassette loxR-hph-loxP was rescued from plasmid JMP115 by I-Sce I digestion and cloned into pGemT-Easy PT at the corresponding I-Sce I site. Selection of the correct clones containing the deletion cassette was done by restriction digestion with EcoRI. Thus the correct pGemT-Easy-PHT plasmid carried the full ylGPI7 deletion cassette containing the hph marker gene. Linear disruption PHT cassettes for GPI7 were generated by PCR amplification from pGemT-Easy-PHT using oligonucleotide primer pair GPI7PF/GPI7TR.

Deletion of gpi7

Yeast cells (Po1d and YIHmA25) were transformed by the lithium acetate method using approximately 1 mg of purified PHT PCR product of the ylgpi7 genes. Ura$^+$ transformants, which appeared after approximately 48 h, were selected on YNBcasa plates. Verification of deletion of the gpi7 gene was confirmed by PCR on genomic DNA of transformants using primer pairs GPI7F/GPI7R. The primer pair GPI7F/GPI7R amplifies the ylGPI7 ORF (2700 bp). GPI7 deletion was further confirmed by Sothern blot analysis, and also by treatment of cells, with substrates that interfere with cell wall assembly (Calcofluor white and Congo red).

Hph Marker Rescue by Expression of Cre Recombinase

To allow excision of the selectable hph marker gene between the two loxP sites, the GPI7::hph strain was transformed with the cre-expressing plasmid, pRRQ2 and selected on YNB5000 plates. Loss of the marker followed by loss of the cre plasmid was achieved by growing the transformants in non-selective YPD broth supplemented with 0.5% (w/v) uracil and 1% (w/v) leucine in two successive 24 h cultures. Δylgpi7 was identified.

Phenotypic Analysis of the Δylgpi7 Strain

The sensitivity of the *Y. lipolytica* Δylgpi7 (YI12) strain and the Po1d control strain to substrates that ordinarily interfere with the cell wall of yeast were tested by growing the strains on YPD plates supplemented with either Calcofluor white (7.5 and 10 μg·mL$^{-1}$) or Congo red (10 μg·mL$^{-1}$ and 15 μg·mL$^{-1}$). Single colonies were selected from the YPD plates and suspended in YPD broth. Serial dilutions of the suspension, $10^{-1}$, $10^{-2}$, $10^{-3}$, $10^{-4}$, $10^{-5}$, $10^{-6}$, and $10^{-7}$ were made. Aliquots (5 μL) from each dilution were streaked onto the Calcofluor white and Congo red YPD agar plates. The plates were incubated for 48 h at 28° C. and 37° C. in order to assay for temperature sensitivity on YPD.

Figure 1:
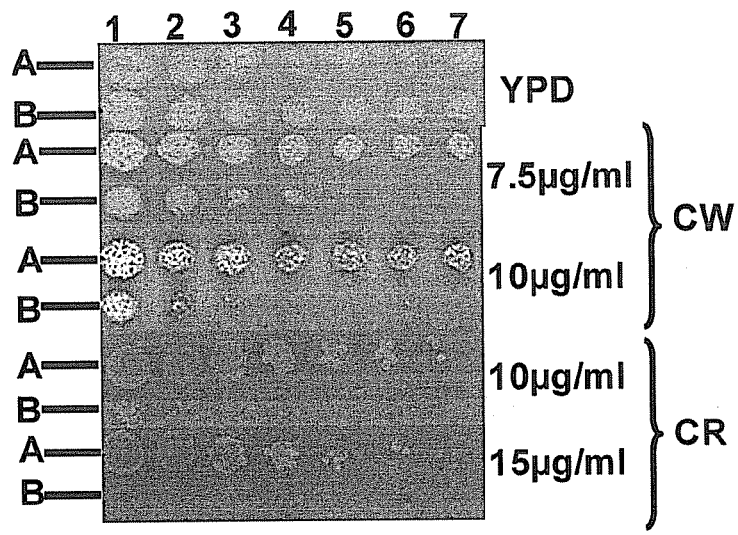
FIG. 1: *Yarrowia lipolytica* Po1d control strain (A) and the *Y. lipolytica* Δylgpi7 (YI12) strain (B) were grown on YPD medium, and YPD medium containing either Calcofluor white (CW) or Congo red (CR). The numbers 1 to 7 represent serial dilutions of the cell suspensions. The plates were incubated at 28° C. for 48 hours.

The *Y. lipolytica* Δylgpi7 (YI12) strain and the Po1d control strain showed similar growth rates on YPD agar medium, however the Y, *lipolytica* Δylgpi7 (YI12) strain exhibited hypersensitivity to Calcofluor white and to Congo red since cells grown on these plates showed reduced growth rates (FIG. 1). The results clearly indicate that the *Y. lipolytica* Δylgpi7 (YI12) strain is sensitive to substrates that interfere with yeast cell wall construction.

Assay for Zymolyase Sensitivity

To test for sensitivity to zymolyase, *Y. lipolytica* Δylgpi7 (YI12) cells and control Po1d cells from exponentially growing cultures were adjusted to an $OD_{600}$ ~1 in 10 mM Tris-HCl (pH 7.5) containing 10 μg zymolyase 20 T, and the decrease in $OD_{500}$ was monitored over a 2 h period. In brief, cells were grown in YPD media until the mid-log phase ($OD_{600}$ 0.3). Cells (5×108) were collected by filtration and resuspended in CE buffer (0.1 M sodium citrate, 10 mM EDTA, adjusted to pH 7.2 with HCl) in glass tubes. After 10 min of treatment with 3% 2-mercaptoethanol, zymolyase was added at a concentration of 5 U·μL$^{-1}$ (Sigma Aldrich, Switzerland) to each tube and the cells were incubated at 30° C. under gentle agitation. Spheroplast lysis after dilution in water was determined by taking measurements at $OD_{600}$, every 15 min using a $DU_{800}$ Beckman spectrophotometer (Beckman Coulter Inc, Brea, United States). The experiment was done in triplicate and the decrease in $OD_{600}$ between readings was taken to indicate cell lysis.

Figure 2:
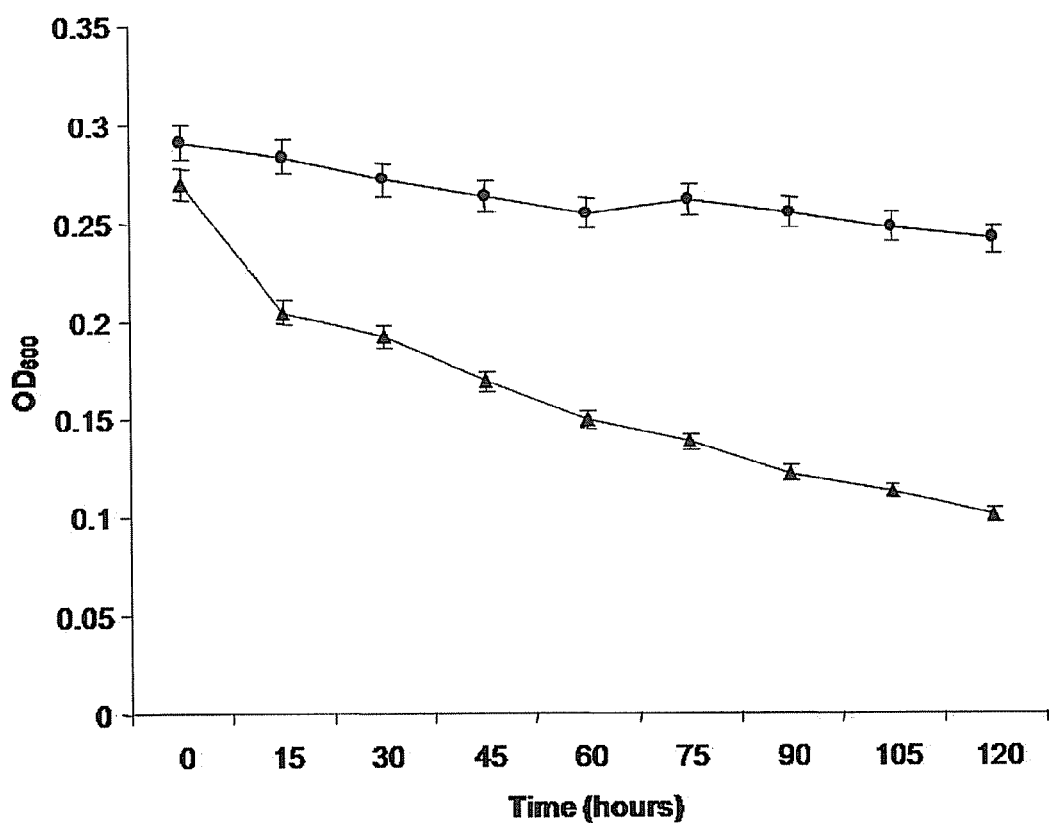
FIG. 2: Zymolyase sensitivity of the *Y. lipolytica* Δylgpi7 (YI12) strain (▲) when compared to the *Y. lipolytica* Po1d control strain (Po1d) (●). Cells exponentially growing on YPD medium at 28° C. were treated with zymolyase. At 15 minute intervals, after the initial addition of the zymolyase enzyme, absorbance was measured after dilution in water. Error bars represent the mean standard deviation calculated from three independent experiments with three samples per experiment.

It was observed that the *Y. lipolytica* Δylgpi7 (YI12) strain demonstrated marked sensitivity to the lytic action of zymolyase as demonstrated by the higher rate of change in absorbance at 600 nm than the *Y. lipolytica* Po1d control strain (FIG. 2).

The Effect of GPI7 Deletion on Cell Separation

To establish if disruption of ylGPI7 in *Y. lipolytica* affects the budding pattern of the cells, the *Y. lipolytica* Po1d control and the Δylgpi7 (YI12) strains were cultured in YPD media and incubated at 28° C. and 37° C. with shaking. Aliquots of both *Y. lipolytica* Po1d control and the Δylgpi7 (YI12) strains growing at 28° C. and 37° C. were withdrawn at the late exponential phase for microscopic observation. Cells were sedimented by transferring 1 mL of the log-phase yeast culture to a microcentrifuge tube and centrifuged at low speed (4000 g) for 1 min. The supernatant was decanted and the cells resuspended in 0.5 ml of fresh YPD medium. The resuspended cells were mounted on microscope slides which were pre-prepared containing agarose cushions comprised of 1.2% (w/v) of agarose in YPD media. The agarose solution was melted in a microwave, and approximately 200 µl of the solution was transferred to a microscope slide prewarmed to 60° C. The agarose-coated slide was covered with a regular microscope coverglass, placed directly onto the agarose, and pressed evenly against the bottom slide. Pure petroleum jelly was applied to the extreme edge of the coverglass. Once the agarose had set the cover slide was removed to expose the agarose cushion by gently pushing the coverglass along the length of the microscope slide. The cell culture resuspensions (2.2 µL) were transferred to the smooth agarose and then covered with a petroleum jelly soaked coverglass. The slide was subjected to live imaging using a Zeiss microscope Axioskop 40 (Carl Zeiss, Inc., North America).

Figure 3:
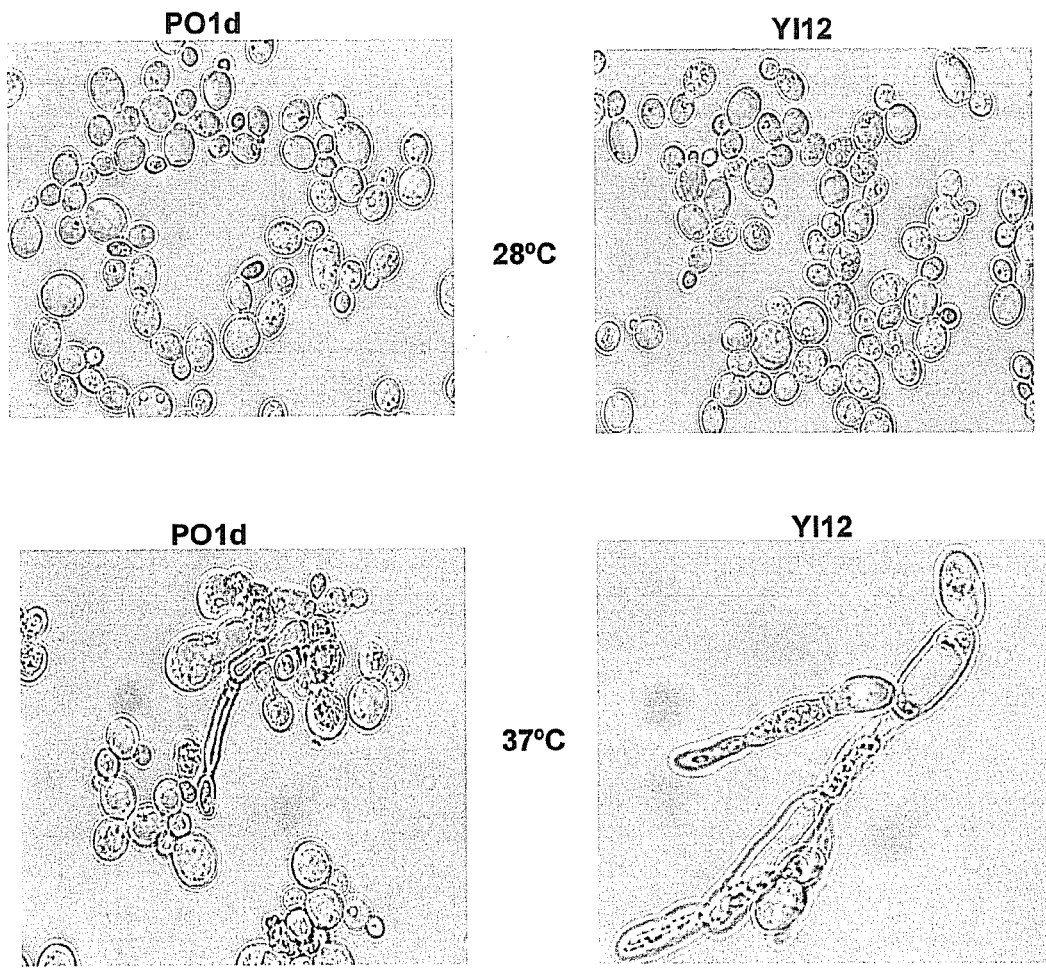
FIG. 3: A Carl Zeiss microimage profile of actively growing cells from the cultures of *Y. lipolytica* Po1d and YI12 strains. The strains were grown in YPD at 28 and 37° C.

It was apparent the daughter cells of the *Y. lipolytica* Δylgpi7 (YI12) strain could not easily separate from the mother cell at 37° C., as compared to the *Y. lipolytica* Po1d control strain (FIG. 3).

Expression of LIP2 in Shake Flask Cultures and the Effect of the GPI7 Deletion on Extracellular LIP2 Secretion Shake flask cultivations were performed in 500 ml Erlenmeyer flasks using the *Y. lipolytica* Po1d control and Δylgpi7 (YI12) strains that had been maintained as cryopreserved cultures at −70° C. Cryovials containing 1.5 mL of the *Y. lipolytica* Po1d control and Δylgpi7 (YI12) strains were used to inoculate triplicate 500 ml Erlenmeyer flasks each containing 100 mL of YPDO medium. Prior to inoculation the pH of the medium was adjusted to 6.8 and autoclaved at 121° C. for 15 min. Erlenmeyer flasks inoculated with the strains were incubated at 28° C. on a rotary shaker at 210 g for a period of 144 h. The growth profile was monitored over the cultivation period and the supernatants were stored at −20° C. for further analyses.

Lipase activity was measured spectrophotometrically using supernatant fractions with p-nitrophenyl palmitate (pNPP) as the substrate according to the method of Winkler and Stuckman (1979). The supernatant of the cell cultures (50 µL), was added to 600 µL of substrate emulsion prepared in a mixture containing 50 mM phosphate buffer, pH 6.8 ($Na_2HPO_4$—$KH_2PO_4$), 0.2% (w/v) sodium deoxycholate, 0.1% (w/v) gum arabic and pNPP (0.30 mM final concentration). Lipase activity was determined by the rate of p-nitrophenol (pNP) production, measured at 410 nm in a model $DU_{600}$ spectrophotometer (Beckman Coulter, Fullerton, Calif.) at 37° C. Lipase activity was assayed using enzyme free substrate blanks as controls. All lipase activity assays were performed in triplicate. One unit of enzyme activity was defined as the amount of enzyme forming 1 µmol of pNP $min^{-1}$ under the mentioned conditions.

Figure 4:
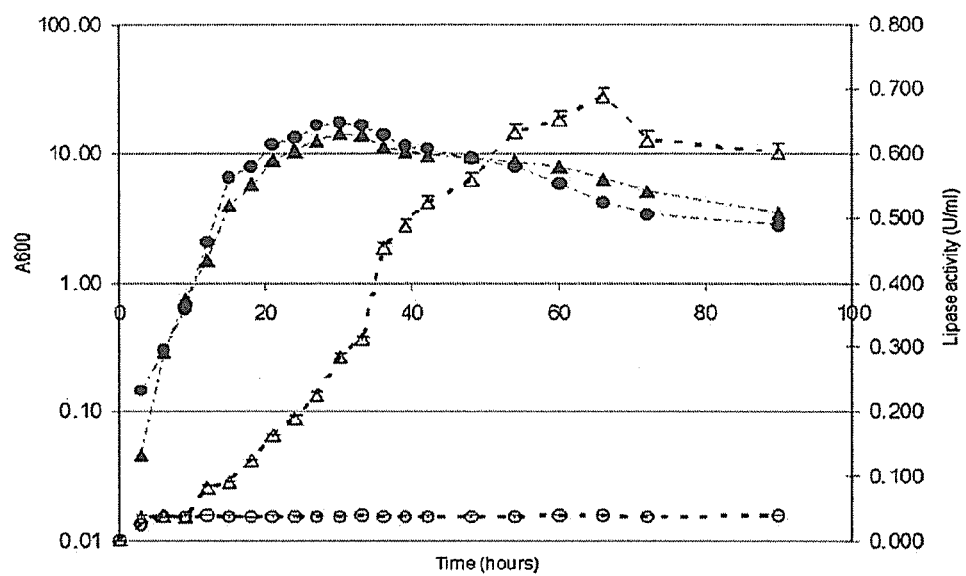
FIG. 4: Production of LIP2 by the *Y. lipolytica* Δylgpi7 (YI12) strain in YPDO. (A) Growth and lipase activity in YPDO medium. Solid circles (●) represent cell growth of the *Y. lipolytica* Po1d control strain (Po1d), whereas cell growth of the *Y. lipolytica* Δylgpi7 (YI12) strain is represented by solid triangles (▲). The extracellular lipase activity profile of the *Y. lipolytica* Po1d control strain is represented by open circles (○) and the extracellular lipase activity profile of the *Y. lipolytica* Δylgpi7 (YI12) strain is represented by open triangles (Δ).
Figure 4:
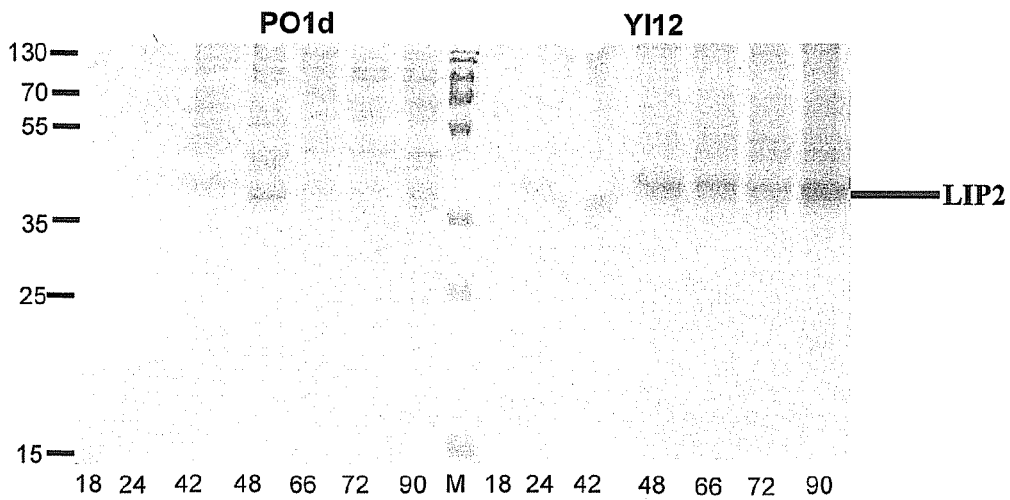

Both the *Y. lipolytica* Po1d control and Δylgpi7 (YI12) strains grew at a similar rate as judged by $OD_{600}$ (~12) measurements (FIG. 4(A)). However, extracellular lipase activity of *Y. lipolytica* Po1d control strain was less than 0.1 $U·mL^{-1}$ as compared to the *Y. lipolytica* Δylgpi7 (YI12) strain which accumulated the maximum of 0.7 $U·mL^{-1}$ lipase activity after 70 hours of cultivation (FIG. 4(A)). SDS-PAGE analysis of the supernatants obtained from the Δylgpi7 (YI12) strain revealed extracellular accumulation of a protein band of about 38.5 kDa, the expected size of the extracellular lipase protein from *Y. lipolytica* (FIG. 4(B)).

Phenotypic Properties of gpi7 Deleted *Y. lipolytica* Strain

The *Y. lipolytica* Po1d and Δylgpi7 (YI12) strain were plated on YNBT agar medium to further assess extracellular lipase activity. The release of extracellular lipase activity as judged by zones of clearance around the yeast colony was higher for the *Y. lipolytica* Δylgpi7 (YI12) strain which displayed a hydrolysis:colony diameter ratio of 1:2.56 while that of the *Y. lipolytica* Po1d control strain was 1:1.3 (FIG. 5). The results indicate that ylGPI7 is indeed implicated in the enhanced release of extracellular lipase activity by the *Y. lipolytica* Δylgpi7 (YI12) strain.

Expression Epoxide Hydrolase (EH) in Shake Flask Cultures and Determination of the GPI7 Deletion on Extracellular EH Activity

*Y. lipolytica* YI25HmA strains (Maharajh et al., 2008) which were genetically engineered to intracellularly express the epoxide hydrolase (EH) enzyme were used to further quantify the effect of the deletion of GPI7 in *Y. lipolytica*. The derivative of the *Y. lipolytica* YI25HmA strain, deleted for GPI7 and denoted *Y. lipolytica* YI25HmAΔGPI7 was constructed to further quantify the extracellular secretion of proteins in *Y. lipolytica* deleted for GPI7. The extracellular production of EH by YI25HmA and YI25HmAΔGPI7 in shake flasks was investigated by assaying EH activity with 1,2-epoxyhexane as the substrate.

Briefly, epoxyhexane was added to a final concentration of 200 mM to 500 µLl of the YIHmA25 and YI25HmAΔGPI7 supernatants (2.5% w/v) in $KH_2PO_4$ buffer [50 mM, pH 7.5 containing 20% (v/v) glycerol]. The reactions were incubated (25° C.) on an Eppendorf shaker with gentle shaking. After 10 min the reactions were stopped with the addition of 500 µL of ethyl acetate for extraction. The samples were vortexed for 30 s and centrifuged in a bench top centrifuge at 13000 g. The organic fractions were dried over anhydrous $MgSO_4$ and analyzed for non-racemic 1,2-epoxyhexane by gas chromatography (GC). Quantitative analysis of 1,2-epoxyhexane bioconversion was performed on a Hewlett Packard 5890 series II gas chromatograph (GC; GMI, MN, USA) equipped with flame ionization detector (FID) and Agilent 6890 series auto sampler injector (GMI), using hydrogen as a carrier gas at a constant column head pressure of 10 psi. The analysis of 1,2-epoxyhexane was achieved using a capillary GC column MDN 5S (Supelco, MS, USA) 30 m length×0.25 mm internal diameter×0.25 µm film thickness, and 10 mM 1-heptanol (Sigma-Aldrich, MS, USA) as the internal standard. Total extracellular proteins were quantified using the Pierce BCA assay using bovine serum albumin (BSA) as the calibrating standard.

GC analysis revealed a peak which corresponded to 1,2-hexanediol only when the substrate was treated with the extracellular fraction derived from the growth culture of the *Y. lipolytica* YI25HmAΔGPI7 strain (FIG. 6). The results indicate the presence of extracellular EH activity in the growth culture of the *Y. lipolytica* YI25HmAΔGPI7 strain.

*Y. lipolytica* YI25HmA and YI25HmAΔGPI7 were also cultured in YPD and their growth profiles and extracellular protein production patterns were compared. The *Y. lipolytica* YI25HmA and YI25HmAΔGPI7 showed similar growth patterns as reflected by $OD_{600}$ measurements (FIG. 7). Analysis of the total extracellular protein from the strains using extracellular supernatants derived from growth cultures of the *Y. lipolytica* YI25HmA and YI25HmAΔGPI7 strains revealed that the YI25HmAΔGPI7 strain produced about 0.6 µg·mL$^{-1}$ extracellular protein as compared to 0.3 µg·mL$^{-1}$ obtained with the YI25HmA strain (FIG. 7).

REFERENCES

Benachour A., Sipos G., Flury I., Reggiori F., Canivenc-Gansel E., Vionnet C., Conzelmann A., Benghezal M. (1999). Deletion of GPI7, a yeast gene required for addition of a side chain to the glycosylphosphatidylinositol (GPI) core structure, affects GPI protein transport, remodeling, and cell wall integrity. *J Biol Chem.* 274:15251-15261.

Madzak, Gaillardin, C., Beckerich J-M (2004) Heterologous protein expression and secretion in the nonconventional yeast *Yarrowia lipolytica*. Yeast 18, 97-113.

Maharajh D., Roth R., Lalloo R., Simpson C., Mitra R., Görgens J., Ramchuran S. (2008). Multi-copy expression and fed-batch production of *Rhodotorula araucariae* epoxide hydrolase in *Yarrowia lipolytica*. *Appl Microbiol Biotechnol.* 79:235-244.

Mauersberger S., Wang H. J., Gaillardin C., Barth G., Nicaud J. M. (2001). Insertional mutagenesis in the n-alkane-assimilating yeast *Yarrowia lipolytica*: generation of tagged mutations in genes involved in hydrophobic substrate utilization. *J Bacteriol.* 183:5102-5109.

Nthangeni M. B., Ramagoma F., Tlou M. G., Litthauer D. (2005). Development of a versatile cassette for directional genome walking using cassette ligation-mediated PCR and its application in the cloning of complete lipolytic genes from *Bacillus* species. *J Microbiol Methods.* 61:225-234.

Winkler U. K., M. Stuckmann. (1979). Glycogen, hyaluronate, and some other polysaccharides greatly enhance the formation of exolipase by *Serratia marcescens*. *J. Bacteriol.* 138: 663-670.

---

The invention claimed is:

1. A composition comprising a *Yarrowia lipolytica*-derived cell population (Accession No. NCIMB 42022, deposited on 9 Aug. 2012 at National Collection of Industrial Food and Marine Bacteria (NCIMB Ltd), of Ferguson Building, Craibstone Estate, Bucksburn, Aberdeen, AB21 9YA, Scotland) capable of expressing a heterologous polypeptide of interest, wherein the level of extracellular secretion of the heterologous polypeptide is increased relative to the level of extracellular secretion of the heterologous polypeptide by a control *Yarrowia lipolytica* cell population (Accession No. NCIMB 42021, deposited on 9 Aug. 2012 at National Collection of Industrial Food and Marine Bacteria (NCIMB Ltd), of Ferguson Building, Craibstone Estate, Bucksburn, Aberdeen, AB21 9YA, Scotland), wherein the *Yarrowia lipolytica*-derived cell population has at least one genomic modification affecting one or more genes involved in glycoslyphosphatidylinositol (GPI) anchoring relative to the control *Yarrowia lipolytica* cell population, wherein the genomic modification is attributable to the increase in extracellular secretion.

2. The composition of claim 1, wherein the *Yarrowia lipolytica*-derived cell population comprises an expression cassette comprising a polynucleotide encoding the heterologous polypeptide.

3. The composition of claim 1, wherein the genomic modification includes the deletion or disruption of the gene encoding GPI7.

4. The composition of claim 1, wherein the level of extracellular secretion of polypeptides from the *Yarrowia lipolytica*-derived cell population is at least two times the level of extracellular secretion from the control *Yarrowia lipolytica* derived cell population.

5. A kit comprising the composition of claim 1.

6. A method of producing a heterologous polypeptide of interest comprising:
   a. obtaining a *Yarrowia lipolytica*-derived cell population (Accession No. NCIMB 42022, deposited on 9 Aug. 2012 at National Collection of Industrial Food and Marine Bacteria (NCIMB Ltd), of Ferguson Building, Craibstone Estate, Bucksburn, Aberdeen, AB21 9YA, Scotland) comprising an expression cassette encoding the heterologous polypeptide of interest; and
   b. culturing the cell population under conditions sufficient for expression of the heterologous polypeptide of interest, wherein the *Yarrowia lipolytica*-derived cell population has at least one genomic modification affecting one or more genes involved in glycoslyphosphatidylinositol (GPI) anchoring relative to a control *Yarrowia lipolytica* cell population (Accession No. NCIMB 42021, deposited on 9 Aug. 2012 at National Collection of Industrial Food and Marine Bacteria (NCIMB Ltd), of Ferguson Building, Craibstone Estate, Bucksburn, Aberdeen, AB21 9YA, Scotland), wherein the genomic modification results in an increase in extracellular secretion of the heterologous polypeptide of interest.

7. A method for increasing the extracellular secretion of polypeptides in *Yarrowia lipolytica* strains wherein the increased extracellular secretion of the polypeptide of interest into a culture medium through the cell membrane is triggered by affecting one or more genes involved in glycosylphosphatidylinositol (GPI) anchoring.

8. The method according to claim 7, wherein the affected gene is the gene encoding GPI7.

9. A recombinant *Yarrowia lipolytica* microorganism genomically modified such that one or more genes involved in glycosylphosphatidylinositol (GPI) anchoring are affected, the microorganism transformed with a recombinant vector comprising a target polypeptide-encoding gene and capable of expressing the target polypeptide for secretion extracellularly, the recombinant microorganism further having a characteristic that at least one gene involved in glycosylphosphatidylinositol (GPI) anchoring is affected and the target polypeptide-encoding gene operates to express the target polypeptide such that the target polypeptide is secreted extracellularly of the microorganism.

10. The recombinant microorganism according to claim 9, wherein the affected gene is the gene encoding GPI7.

11. A method for the extracellular secretion of a target polypeptide, the method comprising the steps of:
   a. culturing the recombinant microorganism according to claim 10, to secrete the target polypeptide to the outside of the microbial cell into culture medium; and
   b. recovering the target polypeptide from the culture medium.

12. The method according to claim 11, wherein the extracellular secretion of the target polypeptide in step (a) does not accompany the lysis of the microorganism.

\* \* \* \* \*